United States Patent
Kashiwagi et al.

(10) Patent No.: US 6,447,494 B1
(45) Date of Patent: Sep. 10, 2002

(54) SANITARY NAPKIN

(75) Inventors: Masahiro Kashiwagi; Hiroyuki Harada; Akiko Ota, all of Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 0 days.

(21) Appl. No.: 09/487,204

(22) Filed: Jan. 19, 2000

(30) Foreign Application Priority Data

Jan. 20, 1999 (JP) ............................................ 11-012514

(51) Int. Cl.[7] .............................................. A61F 13/15
(52) U.S. Cl. ........................ 604/385.03; 380/385.01; 380/385.23; 380/386; 380/389
(58) Field of Search ........................... 604/385.03, 380, 604/385.01, 385.23, 386, 389

(56) References Cited

U.S. PATENT DOCUMENTS 5,171,302 A * 12/1992 Buell .................... 604/385.01
5,545,156 A * 8/1996 DiPalma ................ 604/385.01
5,849,003 A * 12/1998 Olsen ........................ 604/387

FOREIGN PATENT DOCUMENTS

WO    WO-9409737    * 5/1994    ........... A61F/13/15

* cited by examiner

*Primary Examiner*—Rodney M. Lindsey
*Assistant Examiner*—Angela J. Grayson
(74) *Attorney, Agent, or Firm*—Lowe Hauptman Gilman & Berner, LLP

(57) ABSTRACT

A sanitary napkin including a middle region and lateral regions lying adjacent the middle region, and a transversely middle region of the sanitary napkin being configured to have a rigidity lower than that of the lateral regions.

23 Claims, 3 Drawing Sheets

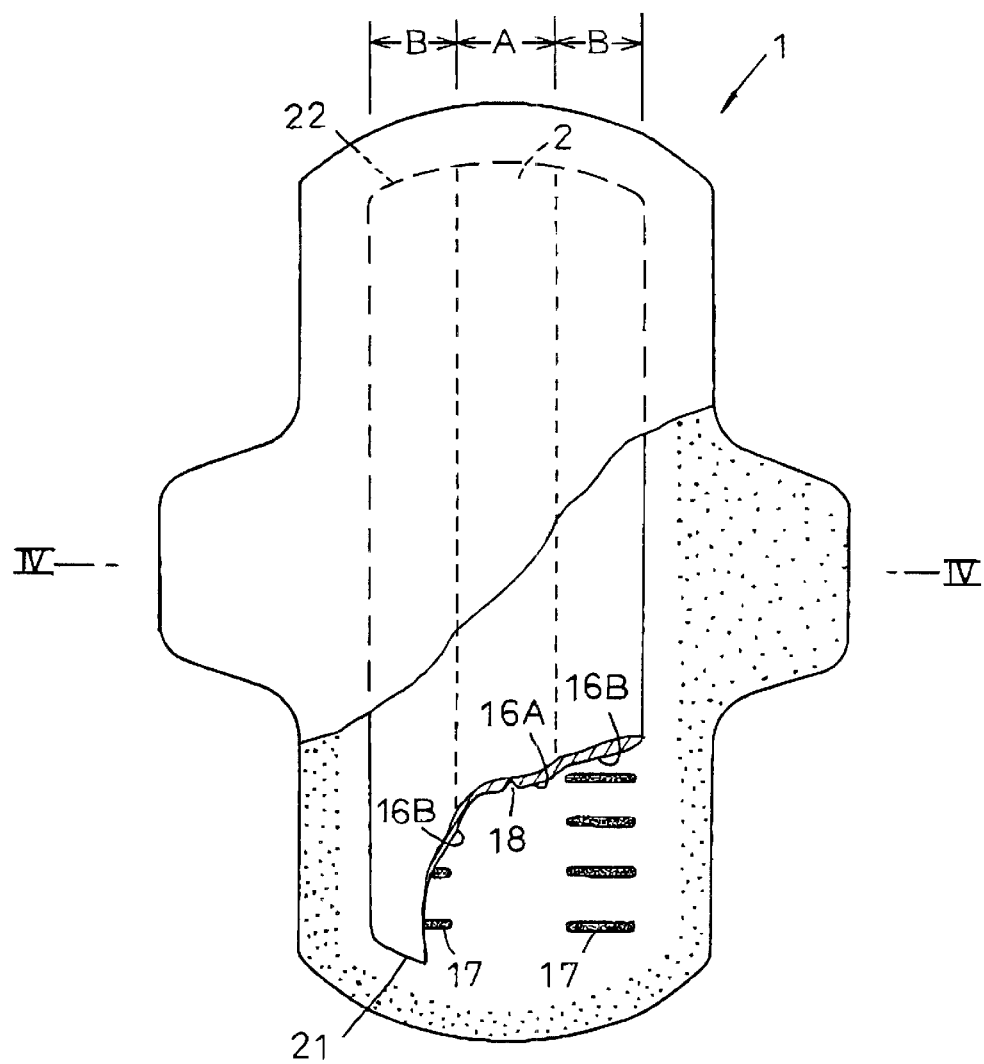

000# SANITARY NAPKIN

BACKGROUND OF THE INVENTION

This invention relates to a sanitary napkin for absorption and containment of menstruation discharge.

There have been made various attempts to improve fitting of a sanitary napkin to the wearer's skin by shaping the liquid-absorbent core to be convex in its transversely middle region.

However, adoption of the convex core is accompanied with considerable labor and time, for example, to shape such convex core and then to place the liquid-pervious topsheet closely upon such convex core. In addition, the napkin adopting such convex core becomes bulky in its convex middle region and it is difficult to stack a plurality of napkins into a compact package. Furthermore, the convex region is resistant against a force intending to fold this region and makes it difficult to fold up the napkin as a whole into a conveniently small size.

SUMMARY OF THE INVENTION

An object of this invention is to provide a sanitary napkin adapted to ensure the same advantageous properties inclusive of a good fitting as the known napkin adopting the convex core can achieve and, in addition, improved to eliminate the problems peculiar to such napkin adopting the convex core.

According to this invention, there is provided a sanitary napkin having a longitudinal direction and a transverse direction intersecting said longitudinal direction, the napkin comprising a liquid-pervious topsheet, a liquid-impervious backsheet and a liquid-absorbent core disposed between the topsheet and the backsheet, a middle region of said napkin in the transverse direction has a rigidity lower than a rigidity of both lateral regions lying adjacent the middle region.

According to one embodiment of this invention, the middle region has a width of 10~30 mm and extends between longitudinally opposite ends of the absorbent core.

According to another embodiment of this invention, the absorbent core is formed on a lower surface of the middle region with a groove of inverted U- or V-shaped cross-section.

According to still another embodiment of this invention, the absorbent core is bonded to an inner surface of the backsheet over portions of the backsheet underlying the both lateral regions, leaving a portion of the backsheet underlying the middle region free.

According to further another embodiment of this invention, a lower surface of the absorbent core is bonded to the inner surface of the backsheet by means of a plurality of adhesive applied spots extending transversely of the napkin and arranged intermittently in a longitudinal direction thereof.

According to an additional embodiment of this invention, an outer surface of the backsheet except a portion thereof underlying the middle region of the absorbent core is adapted to be adhesively fastened to an undergarment.

BRIEF DESCRIPTION OF THE DRAWINGS

FIG. 3 is a view similar to FIG. 1 showing another embodiment of this invention;

DETAILED DESCRIPTION OF THE PREFERRED EMBODIMENTS

A sanitary napkin according to this invention will be described in more detail by way of example with reference to the accompanying drawing.

Figure 1:
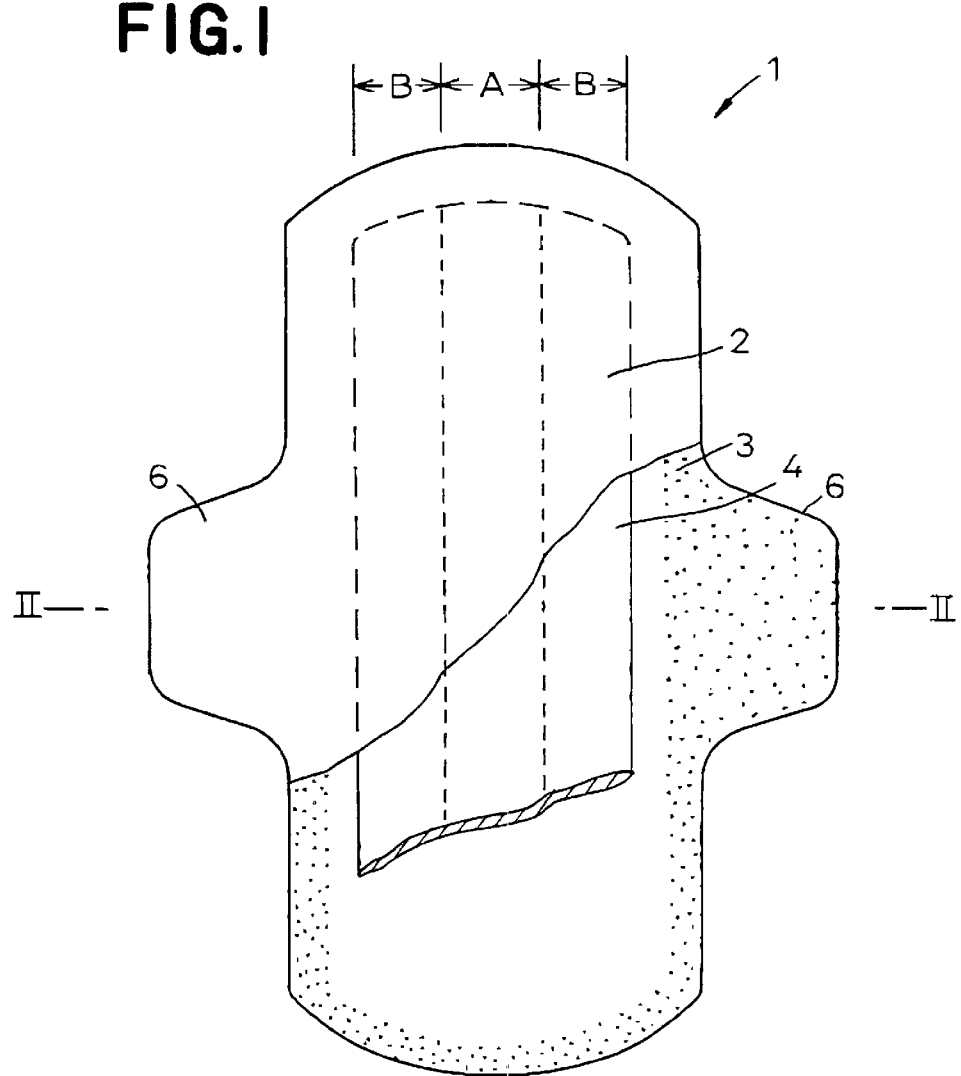
FIG. 1 is a perspective view showing an embodiment of a partially cutaway sanitary napkin according to this invention.

A sanitary napkin 1 shown by FIG. 1 in a perspective view as partially broken away is configured to be relatively elongate in a back-and-forth direction with respect to a wearer and comprises a liquid-pervious topsheet 2 formed by a nonwoven fabric of thermoplastic synthetic fibers, a backsheet 3 formed by a thermoplastic synthetic resin film and a liquid-absorbent core 4 containing 40% by weight or higher of fluff pulp and disposed between the two sheets 2, 3. The topsheet 2 and the backsheet 3 are put flat together and bonded to each other at a plurality of spots over their peripheral portions extending outward beyond a peripheral edge of the absorbent core 4 by means of hot melt adhesive agent or suitable sealing technique. In a longitudinally middle region of the napkin 1, the topsheet 2 and the backsheet 3 further extend laterally from the peripheral portions to form a pair of wings 6.

Figure 2:
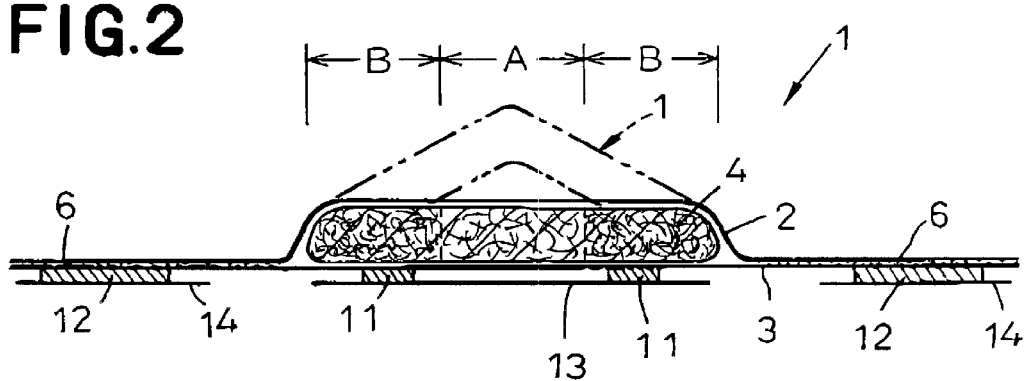
FIG. 2 is a sectional view taken along a line II—II in FIG. 1.

FIG. 2 is a sectional view taken along a line II—II in FIG. 1. The absorbent core 4 comprises a middle region A and lateral regions B, B lying adjacent the middle region A as viewed transversely of the napkin 1 (See FIG. 1 also). The middle region A has a thickness equal to or slightly larger than a thickness of the lateral regions B, B and a density lower than a density of the lateral regions B, B so that the middle region has a rigidity lower than a rigidity of the lateral regions B, B as the absorbent core 4 is bent in its transverse direction. The middle region A is preferably dimensioned to be in a range of 1–30 mm and each of the lateral regions B, B is preferably dimensioned also to be in the range of 10–30 mm. The absorbent core 4 may be obtained, for example, by forming both the middle region A and the lateral regions B, B so as to be of the same composition and then compressing the lateral regions so as to present a density higher than a density of the middle region A. Portions of the backsheet 3 overlapping the lateral regions B, B of the absorbent core 4 as well as portions of the backsheet 3 defining the wings 6 are formed on their outer surfaces with adhesive fastening zones 11, 11; 12, 12 used to fasten the napkin 1 to an undergarment. The adhesive fastening zones 11, 11; 12, 12 are protected by release sheets 13, 14. With the napkin 1 arranged in the manner as has been described above, a portion of the backsheet 3 overlapping the middle region A of the absorbent core 4 is not fastened to the undergarment.

Figure 4:
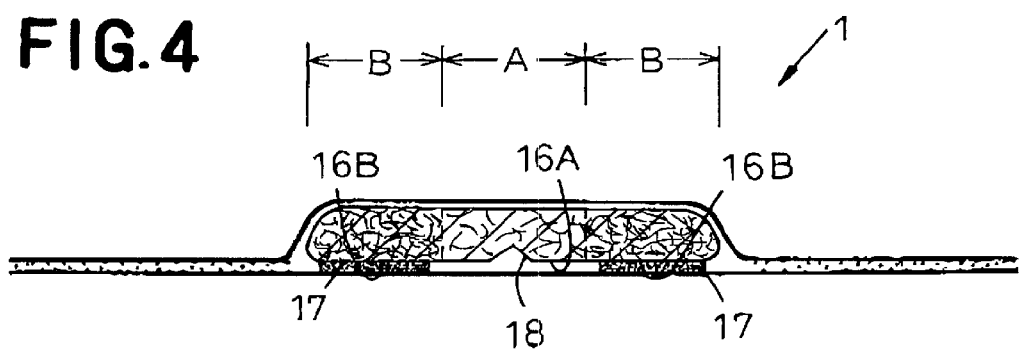
FIG. 4 is a sectional view taken along a line IV—IV in FIG. 3.

FIGS. 3 and 4 are views respectively similar to FIGS. 1 and 2 showing another embodiment of this invention. According to this embodiment of the napkin 1, the bottom surface of the absorbent core 4 is bonded to the inner surface of the backsheet 3 along portions 16B, 16B of the bottom surface underlying the respective lateral regions B, B by means of a plurality of adhesive applied spots 17 extending transversely of the absorbent core 4 and arranged intermittently in the longitudinal direction of the napkin 1. A portion 16A of the bottom surface underlying the middle region A is formed with a groove 18 of inverted U- or V-shaped cross-section. The groove 18 extends to longitudinally opposite ends 21, 22 of the absorbent core 4.

The sanitary napkin 1 according to the embodiments illustrated by FIGS. 1–4 is deformed in an inverted U- or V-shape with an apex defined by the middle region A having a relatively low rigidity and moved into close contact with the wearer's skin as the napkin 1 is fastened to the undergarment and compressed from its both sides (as indicated by imaginary lines in FIG. 2). The deformation of the napkin 1 in the inverted V- or U-shaped with the apex defined by the middle region A is facilitated particularly by the adhesive spots 17 extending transversely of the napkin 1 and arranged intermittently in the longitudinal direction thereof. The deformation is further facilitated by the groove 18 of the inverted V- or U-shaped cross-section. The adhesive applied spots 17 are preferably dimensioned to be 0.5–10 mm as measured in the longitudinal direction of the napkin 1 and preferably spaced one from another by 5–80 mm longitudinally of the napkin 1. It is also possible to arrange the adhesive applied spots 17 so that the spots 17 extend longitudinally of the napkin 1 and are spaced one from another transversely of the napkin 1. The groove 18 preferably has a depth corresponding to ¼~⅘ of a thickness of the absorbent core 4 and has a width of 5–20 mm.

Figure 5:
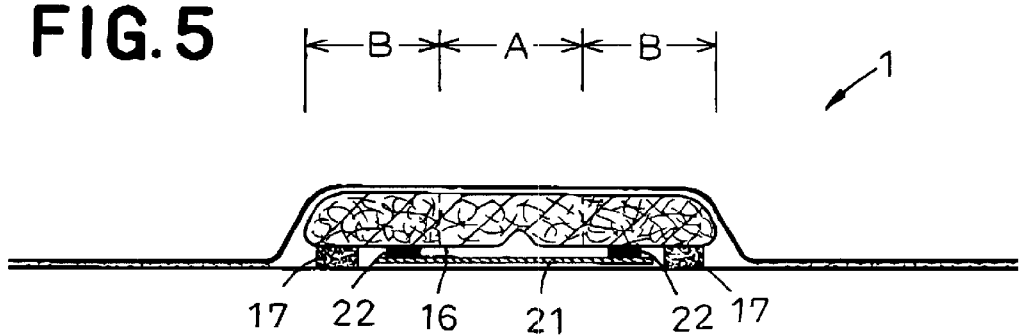
FIG. 5 is a view similar to FIG. 4 showing still another embodiment of this invention.

FIG. 5 is a view similar to FIG. 4 showing still another embodiment of this invention. According to this embodiment, an elastic member 21 transversely extends across the middle region A and bonded under tension to the lower surface 16 of the absorbent core 4 or the outer surface of the backsheet 3 by means of hot melt adhesive agent 22, 22. The napkin 1 is easily deformed into the inverted V-shape as the elastic member 21 contracts.

The absorbent core 4 in the napkin 1 according to this invention may contain 60% by weight or less of superabsorptive polymer particles and 20% by weigh or less of thermoplastic synthetic fibers.

The sanitary napkin according to this invention is characterized in that its transversely middle region has a relatively low rigidity. Therefore, the napkin is easily deformed with the apex defined by the upper surface of the middle region as the napkin is compressed from its both sides. Even when the absorbent core is not convex and relatively planar, a good fitting of the napkin to the wearer's body is ensured.

Production of such napkin is relatively easy and a stack of these napkins can be packaged in compact condition.

What is claimed is:

1. A sanitary napkin having a longitudinal direction and a transverse direction intersecting said longitudinal direction, said napkin comprising a liquid-pervious topsheet, a liquid-impervious backsheet and a liquid-absorbent core disposed between said topsheet and said backsheet, and a middle region of said napkin in said transverse direction having a rigidity lower than a rigidity of both lateral regions lying adjacent said middle region.

2. The napkin according to claim 1, wherein said middle region has a width of 10~30 mm and extends between longitudinally opposite ends of said absorbent core.

3. The napkin according to claim 1, wherein said absorbent core is formed on a lower surf ace of said middle region with a groove of inverted U- or V-shaped cross-section.

4. The napkin according to claim 1 , wherein said absorbent core is bonded to an inner surface of said backsheet over portions of said backsheet underlying said both lateral regions, leaving a portion of said backsheet underlying said middle region free.

5. The napkin according to claim 4, wherein a lower surface of said absorbent core is bonded to the inner surface of said backsheet by means of a plurality of adhesive applied spots extending transversely of said napkin and arranged intermittently in a longitudinal direction thereof.

6. The napkin according to claim 1, wherein an outer surface of said backsheet except a portion thereof underlying said middle region of said absorbent core is adapted to be adhesively fastened to an undergarment.

7. The napkin according to claim 1, wherein a density of the absorbent core in the middle region is lower than in the lateral regions.

8. The napkin according to claim 7, wherein the absorbent core in the middle region and in the lateral regions is first made of the same composition with the lateral regions of the absorbent core being then compressed to be higher in density than the middle region thereof.

9. The napkin according to claim 1, further comprising an elastic member which is provided between a lower surface of the absorbent core and the backsheet to span over the middle region and bonded to the lower surface of the absorbent core in the lateral regions.

10. The napkin according to claim 9, wherein the elastic member is bonded under tension to the lower surface of the absorbent core so that the napkin is easily deformed into a generally inverted V-shape as the elastic member contracts.

11. The napkin according to claim 10, wherein the elastic member is not bonded to the lower surface of the absorbent core in the middle region.

12. A sanitary napkin having a longitudinal direction and a transverse direction intersecting said longitudinal direction, said napkin comprising a liquid-pervious topsheet, a liquid-impervious backsheet and a liquid-absorbent core disposed between said topsheet and said backsheet, a middle region of said absorbent core in said transverse direction having a rigidity lower than a rigidity of both lateral regions lying adjacent to and at opposite sides of said middle region.

13. The napkin according to claim 12, wherein said middle region has a width of from about 10 to about 30 mm and extends between longitudinally opposite ends of said absorbent core.

14. The napkin according to claim 12, wherein said absorbent core is formed on a lower surface of said middle region with a groove of inverted U- or V-shaped cross-section.

15. The napkin according to claim 12, wherein said absorbent core is bonded to an inner surface of said backsheet in portions of said backsheet underlying said lateral regions, said absorbent core is not bonded to the inner surface of said backsheet a portion of said backsheet underlying said middle region.

16. The napkin according to claim 15, wherein a lower surface of said absorbent core is bonded to the inner surface of said backsheet by means of a plurality of adhesive applied spots extending transversely of said napkin and arranged intermittently in the longitudinal direction thereof.

17. The napkin according to claim 15, wherein an outer surface of said backsheet except a portion thereof underlying said middle region of said absorbent core is provided with adhesive fastening zones adapted to be adhesively fastened to an undergarment.

18. The napkin according to claim 12, wherein a density of the absorbent core in the middle region is lower than in the lateral regions.

19. The napkin according to claim 18, wherein the absorbent core in the middle region and in the lateral regions is first made of the same composition with the lateral regions of the absorbent core being then compressed to be higher in density than the middle region thereof.

20. The napkin according to claim 12, further comprising an elastic member which is provided between a lower surface of the absorbent core and the backsheet to span over the middle region and bonded to the lower surface of the absorbent core in the lateral regions.

21. The napkin according to claim 20, wherein the elastic member is bonded under tension to the lower surface of the absorbent core so that the napkin is easily deformed into a generally inverted V-shape as the elastic member contracts.

22. The napkin to claim 21, wherein the elastic member is not bonded to the lower surface of the absorbent core in the middle region.

23. The napkin according to claim 12, wherein a density of the absorbent core in the entire middle region is lower than in the entire lateral regions.

* * * * *